US008503759B2

(12) United States Patent
Greer et al.

(10) Patent No.: US 8,503,759 B2
(45) Date of Patent: Aug. 6, 2013

(54) METHODS, DEVICES, AND SYSTEMS USEFUL IN REGISTRATION

(76) Inventors: Alexander Greer, Calgary (CA); Garnette Sutherland, Calgary (CA); Tim Fielding, Brampton (CA); Perry Newhook, Caledon (CA); Scott King, Winnipeg (CA); Calvin Bewsky, Winnipeg (CA); Jarod Matwiy, Winnipeg (CA); Boguslaw Tomanek, Calgary (CA); Mike Smith, Winnipeg (CA)

( * ) Notice: Subject to any disclaimer, the term of this patent is extended or adjusted under 35 U.S.C. 154(b) by 634 days.

(21) Appl. No.: 12/596,397

(22) PCT Filed: Apr. 16, 2008

(86) PCT No.: PCT/IB2008/003353
§ 371 (c)(1),
(2), (4) Date: Jul. 30, 2010

(87) PCT Pub. No.: WO2009/040677
PCT Pub. Date: Apr. 2, 2009

(65) Prior Publication Data
US 2010/0296723 A1    Nov. 25, 2010

Related U.S. Application Data

(60) Provisional application No. 60/912,140, filed on Apr. 16, 2007, provisional application No. 60/912,169, filed on Apr. 17, 2007.

(51) Int. Cl.
*G06K 9/00* (2006.01)
*G06K 9/36* (2006.01)
*A01B 5/103* (2006.01)
*G06F 19/00* (2011.01)

(52) U.S. Cl.
USPC ........... 382/153; 382/100; 382/287; 600/595; 700/245

(58) Field of Classification Search
USPC ................. 382/153, 154, 100, 152, 131, 132, 382/276, 287, 285; 600/300, 587, 595, 103, 600/437, 414, 422, 426, 427, 248; 604/95.01, 604/48, 19, 93.01; 700/245, 248, 247, 249
See application file for complete search history.

(56) References Cited

U.S. PATENT DOCUMENTS

| | | | |
|---|---|---|---|
| 6,198,961 B1 | 3/2001 | Stern et al. | 600/422 |
| 6,236,875 B1 * | 5/2001 | Bucholz et al. | 600/407 |
| 6,246,900 B1 | 6/2001 | Cosman et al. | 600/426 |
| 6,314,310 B1 | 11/2001 | Ben-Haim et al. | 600/427 |
| 6,591,128 B1 | 7/2003 | Wu et al. | 600/422 |
| 7,155,316 B2 * | 12/2006 | Sutherland et al. | 700/248 |
| 7,620,144 B2 * | 11/2009 | Bodduluri | 378/41 |
| 2005/0054910 A1 | 3/2005 | Tremblay et al. | 600/414 |
| 2007/0276234 A1 * | 11/2007 | Shahidi | 600/437 |

OTHER PUBLICATIONS

Written Opinion and International Search Report issued in PCT/IB2008/003353 dated Aug. 14, 2009.

* cited by examiner

*Primary Examiner* — Sheela Chawan
(74) *Attorney, Agent, or Firm* — Fulbright & Jaworski LLP

(57) ABSTRACT

Methods, devices, and systems for use in accomplishing registration of a patient to a robot to facilitate image guided surgical procedures, such as stereotactic procedures.

6 Claims, 13 Drawing Sheets

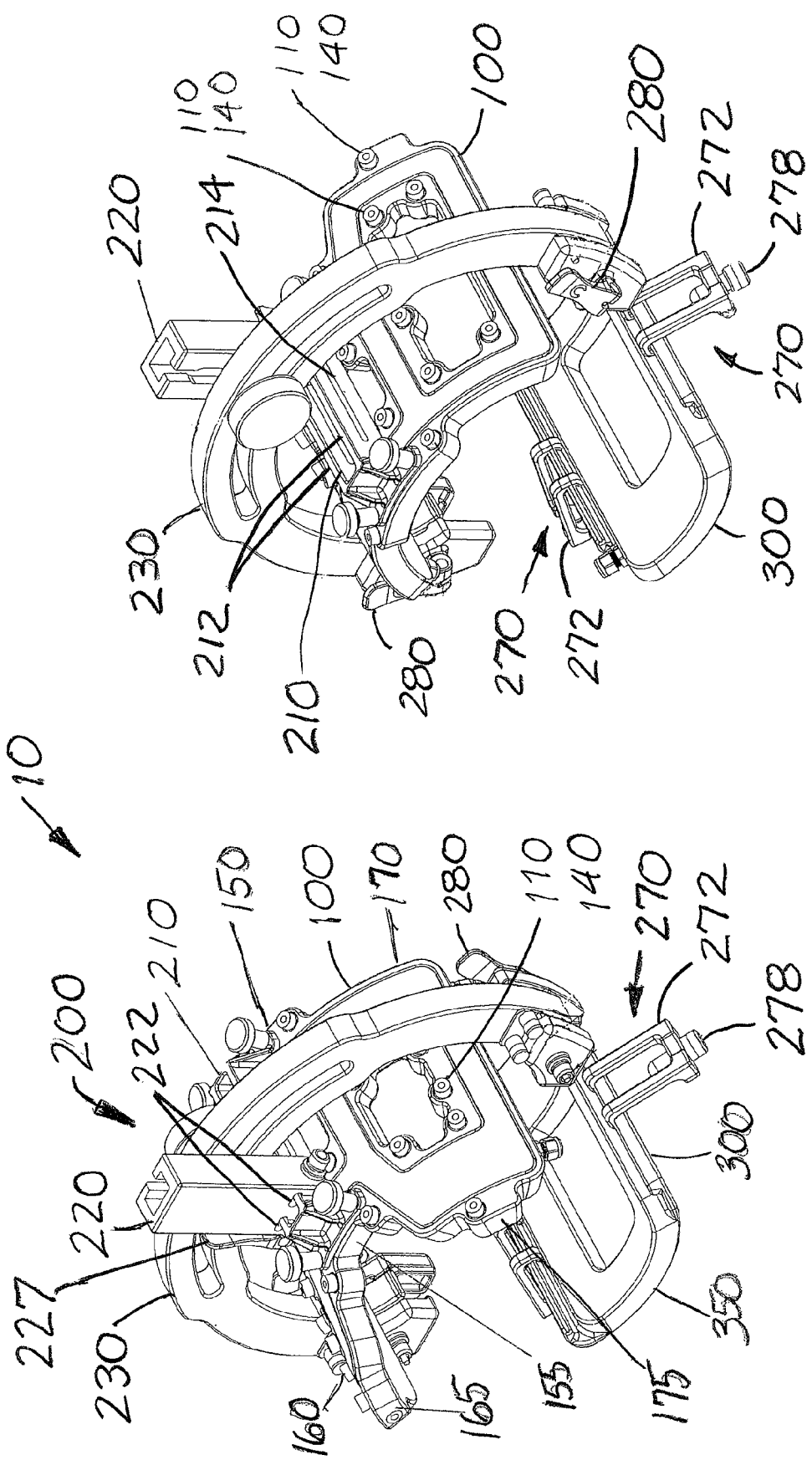

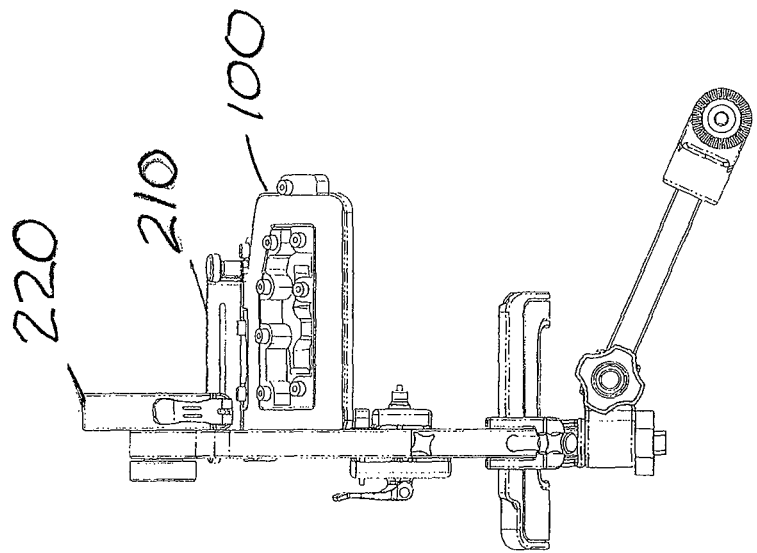
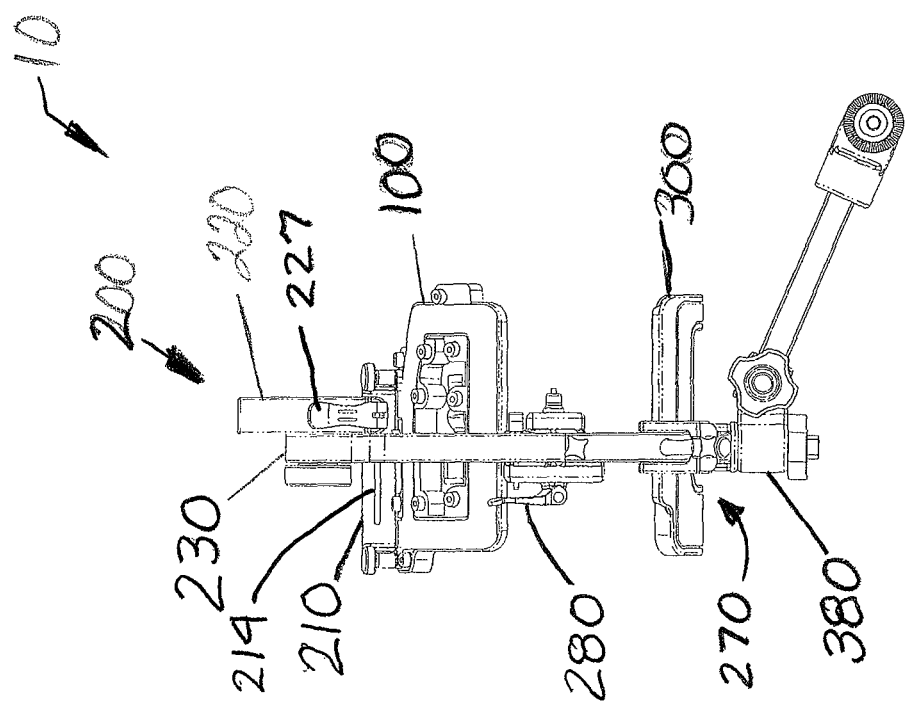
FIG. 9B
FIG. 9A

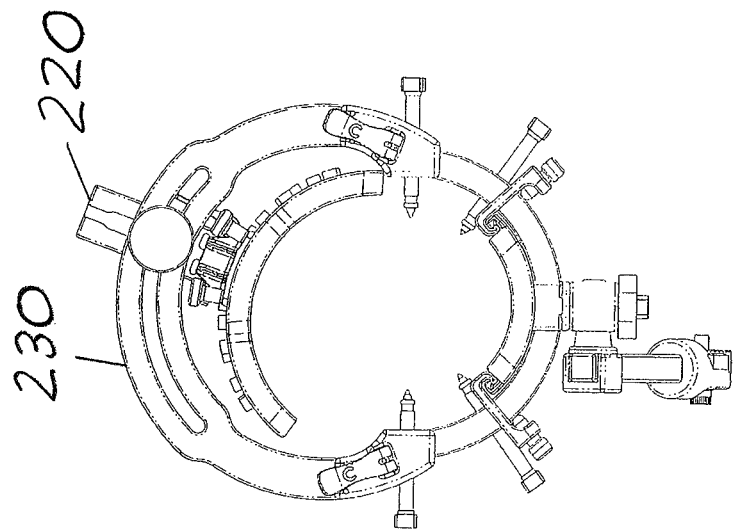
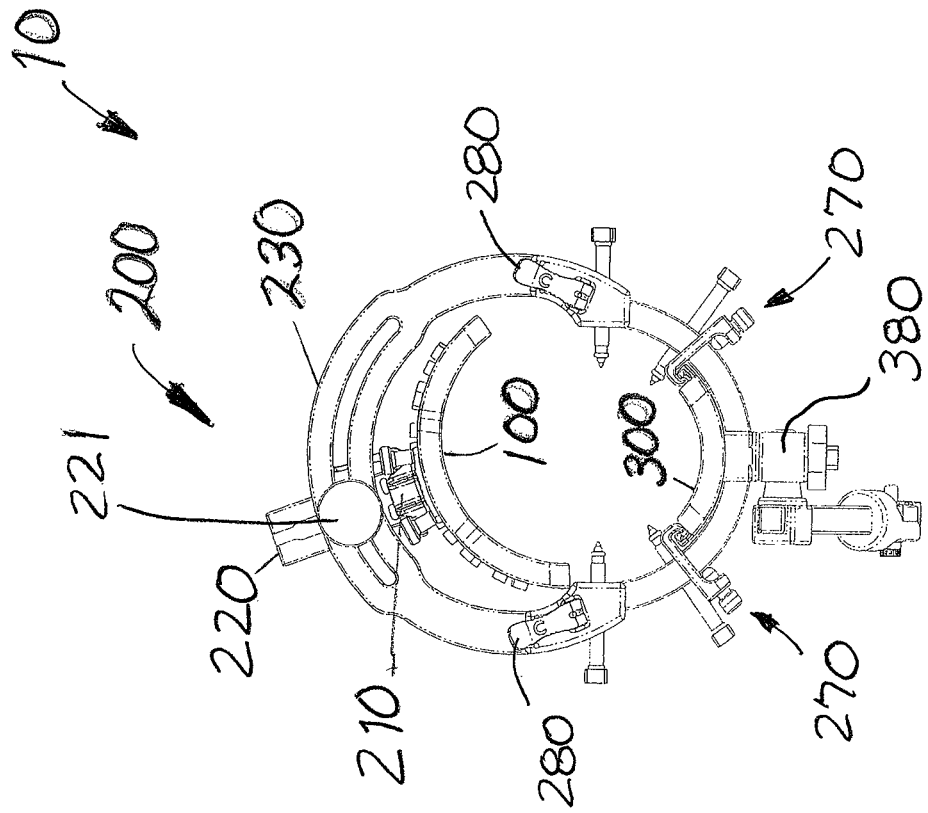

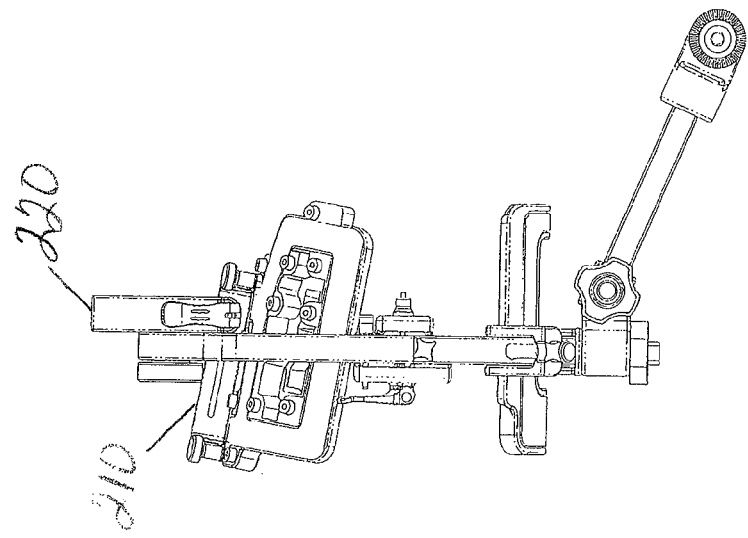
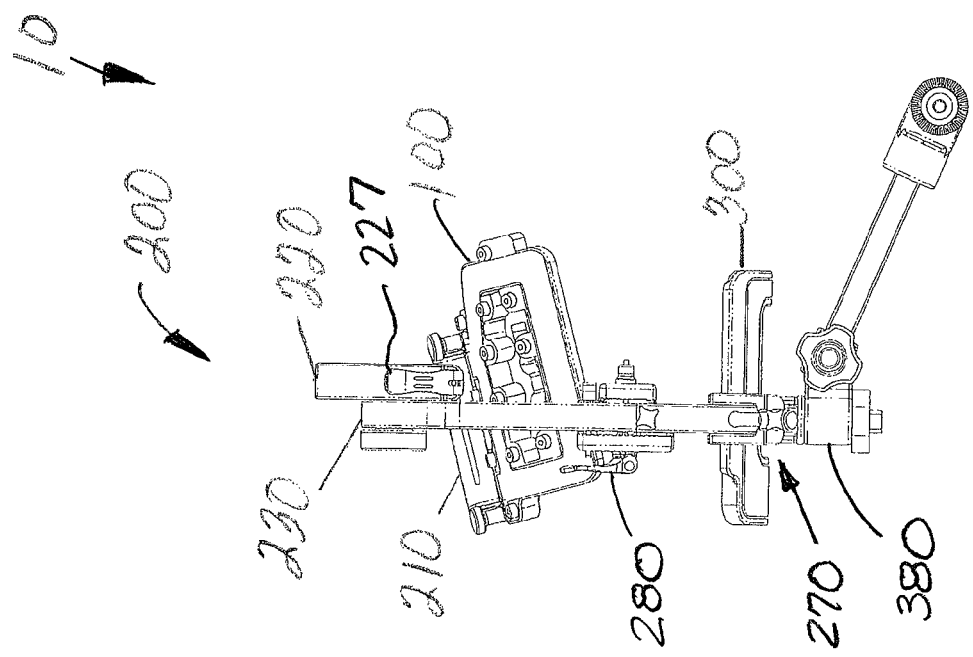

METHODS, DEVICES, AND SYSTEMS USEFUL IN REGISTRATION

CROSS REFERENCE TO RELATED APPLICATIONS

This application is a national phase application under 35 U.S.C. §371 of International Application No. PCT/IB2008/003353, filed Apr. 16, 2008, which claims priority to U.S. Provisional Patent Application Ser. No. 60/912,140, filed Apr. 16, 2007, and to U.S. Provisional Patent Application Ser. No. 60/912,169, filed Apr. 17, 2007, the entire contents of each of which are incorporated by reference.

BACKGROUND

The present methods, devices, and systems relate generally to the field of image guided surgery, and with the registration of one or more patient images to an object (such as a tool or instrument, and more particularly a surgical tool or instrument) relevant to the procedure. An example of a surgical robot that can be used in a procedure to which the present registration methods, devices, and systems relate is disclosed in U.S. Pat. No. 7,155,316, which is incorporated by reference. Examples of registration techniques, not necessarily associated with surgical robots, are included in U.S. Patent Application Publication No. US 2005/0054910 A1, which is incorporated by reference.

SUMMARY

In one respect, the present techniques (which may take the form of methods) relate to registering an image of an object, such as a patient, to a robotic arm such that it is possible to superimpose a representation of an instrument (such as a surgical instrument) of the robotic arm (such as an instrument that is held by or integral with the robotic arm), such as one of the robotic arms disclosed in the '316 patent, over a 3D image of a portion of the object (such as a portion of a patient's anatomy). The superimposition may occur as a procedure is performed such that an operator of the surgical robot (of which the robotic arm is a part) can use the display showing that superimposition as a guide during the procedure.

In one respect, the present devices comprise a radio frequency (RF) coil device that allows free access, for example, for a surgery, robotic arms, or the like. The RF coil device may contain pockets, such as recesses, that can receive and at least partially surround fiducial markers (e.g., one marker to a pocket). In some embodiments, a pocket or pockets containing a fiducial marker (e.g., a vitamin E capsule) can be sealed (e.g., using at least a cap containing a touch point configured for contact by a registration tool such as a digitizing arm) for gaseous or liquid submersion sterilization procedures. The RF coil device can be made of a material that allows any type of sterilization. In some embodiments the device may be configured to be sterilized such that it can be positioned relative to a patient with an open lesion such that the portion of the device closest to the open lesion is less than 50 centimeters from the lesion in some embodiments, less than 40 centimeters in some embodiments, less than 30 centimeters in some embodiments, less than 20 centimeters in some embodiments, less than 10 centimeters in some embodiments, and about 5 centimeters in some embodiments. The RF coil device may be configured such that, when attached to an operating table or to a structure that is coupled to an operating table, at least a portion of it can be moved in multiple (e.g., four) directions, such as up-down (which may be referred to as anterior-posterior translation), head-foot (which may be referred to as superior-inferior translation), rotate, and tilt.

The RF coil device may be configured to focus signal-to-noise performance in the selected surgical region of interest. Any touch point features that are provided on the RF coil device may be adjacent to (e.g., in close proximity to) a given fiducial marker. The RF coil device may be configured to be attached to a head holder for brain surgery or any other holder for other surgeries such as cardiac, knee spine, etc. Thus, the RF coil device may be used with: an intraoperative magnetic resonance imaging (MRI) system, most robotic arms for surgery (on any part of the body), standard magnetic resonance (MR) imaging for versions of the RF coil device having a very high sensitivity in a specific region in combination with a head holder in brain surgery, and image-guided systems.

In another respect, the present devices may include an RF coil device releasably coupled to head clamp.

Other features and embodiments of the present methods and devices are described below and/or shown in the accompany drawings.

Any embodiment of any of the present methods, devices (e.g., computer readable media), and systems (e.g., computer systems) may consist of or consist essentially of—rather than comprise/include/contain/have—the described functions, steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE DRAWINGS

The following drawings illustrate by way of example and not limitation. Identical reference numerals do not necessarily indicate an identical structure, system, or display. Rather, the same reference numeral may be used to indicate a similar feature or a feature with similar functionality. Every feature of each embodiment is not always labeled in every figure in which that embodiment appears, in order to keep the figures clear. The hand controllers, manipulators, RF coil devices, and head clamps shown in the figures are drawn to scale, meaning the sizes of the depicted elements are accurate relative to each other.

FIG. 8: is a perspective view an RF coil device having an attachment mechanism that allows four degree-of-freedom adjustment of a first structure.

FIGS. 9A and 9B depict adjustment of an RF coil device in which the first structure is translated in the head-foot direction of the patient.

FIGS. 11A and 11B depict adjustment of an RF coil device in which the first structure is rotated aximuthally.

FIGS. 12A and 12B depict adjustment of an RF coil device in which the first structure is tilted.

DESCRIPTION OF ILLUSTRATIVE EMBODIMENTS

Figure 1:
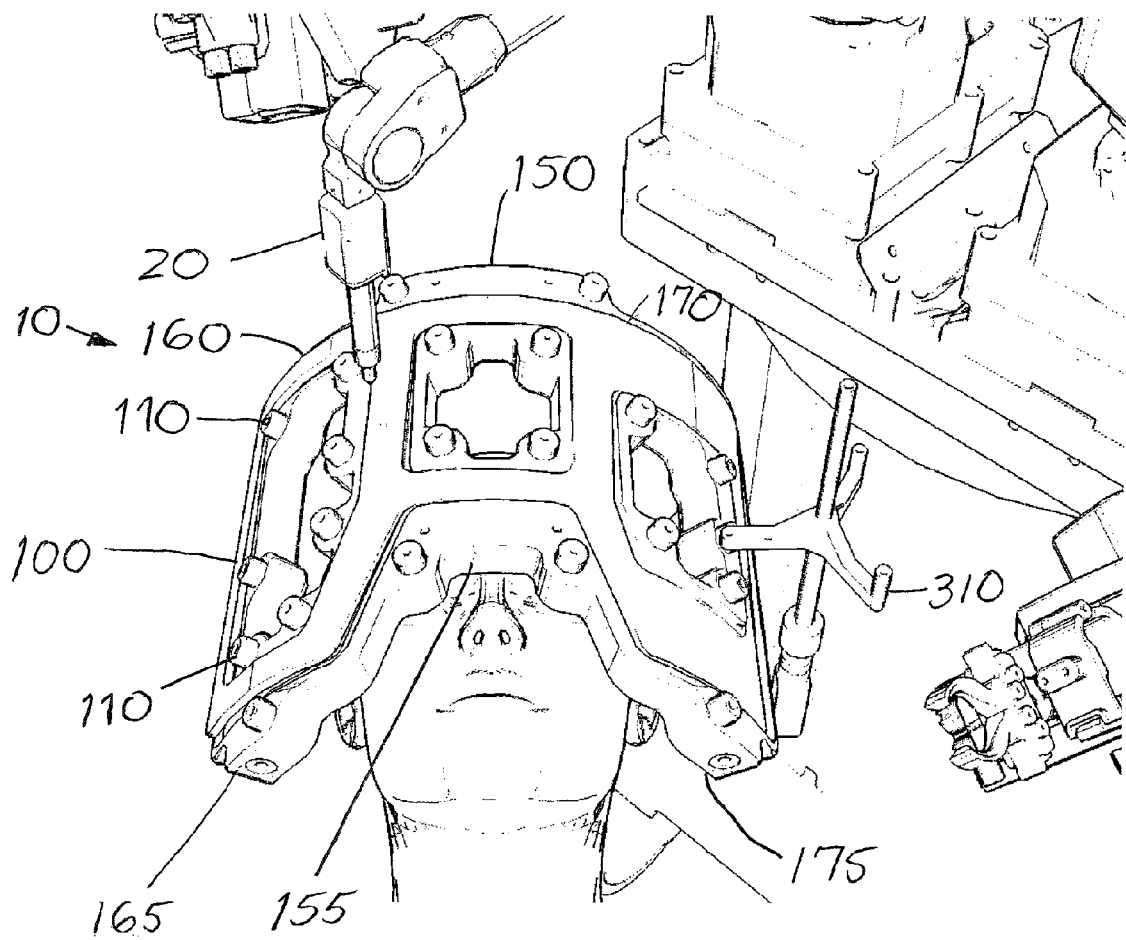
FIGS. 1-3 are views showing an RF coil device and a registration arm of a registration tool.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. Thus, a method comprising certain steps is a method that includes at least the recited steps, but is not limited to only possessing the recited steps. Similarly, a computer readable medium "comprising" machine readable instructions for performing certain steps is a computer readable medium that has machine readable instructions for implementing at least the recited steps, but also covers media having machine readable instructions for implementing additional, unrecited steps. Further, a computer system that is configured to perform at least certain functions is not limited to performing only the recited functions.

The terms "a" and "an" are defined as one or more than one, unless this application expressly requires otherwise. The term "another" is defined as at least a second or more. The terms "substantially" and "about" are defined as at least close to (and includes) a given value or state (preferably within 10% of, more preferably within 1% of, and most preferably within 0.1% of).

As part of a surgical procedure involving a surgical robot that will involve operator use of image guidance, a registration process may be used to determine the positioning (e.g, the substantially precise positioning) of various components (such as those that are most important to the performance of the procedure) relative to each other. A registration process may allow positions that are known relative to varying specific components to be mapped to a common reference environment, or "workspace." For example, the use of absolute encoders and the calculation of the system kinematics may allow for the determination of a surgical robot's end effector position relative to the base of the robot. Similarly, the position of a patient's anatomical features relative to a device fixed to the patient's head may be known with accuracy. However, the location of the base of the robot relative to the device fixed to the patient's head may vary from procedure to procedure, and therefore be unknown. The present registration processes facilitate expression of the robot's position data and the patient's anatomical data in the same workspace. As a result, the position of a surgical tool (which also may be characterized as a surgical instrument) carried by or integrated with a robotic arm (also characterized as a manipulator in this disclosure) of the surgical robot that is taken from the values representing the positions of the joints of the robotic arm may be used to overlay a virtual representation of the tool on a volume rendering of a 3D image of the patient (e.g., one taken using an MRI machine) on a display visible to the operator of the robot. In turn, the operator can drive the manipulator to a specific point in, for example, the patient's head using that overlayed tool position as a reference.

In some embodiments, two stages of registration—physical and MRI—can be performed to achieve this. In some embodiments, the physical registration involves a user selecting physical touch point features on one or both of the manipulators, on a structure (e.g., a rigid structure, sometimes referred to as a first structure) attached to an RF coil that can be secured to the head of the patient, and on a secondary target (which can also be rigid, and which is sometimes referred to as a second structure) attached to the RF coil. Throughout this disclosure, a touch point that is "on" an object is one that is integrated with or otherwise connected to that object. Generally, a touch point includes a feature (such as a divot or a bump) that can be contacted by a tip of registration tool. In some embodiments, the MRI registration involves a user identifying/selecting markers embedded in the first structure that appear in images taken of the patient (when the RF coil device and the first structure are secured to the patient's head) using an imaging device such as an MRI system (whether open or closed bore).

In some embodiments, the registration process can compute the transformation between a coordinate space of the manipulator(s) and a coordinate space of the first structure and the transformation from the coordinate space of the first structure to the MRI image coordinate space. In this disclosure, coordinate space and coordinate system are synonyms. These transformations allows for data in the manipulator coordinate space, such as tool tip position based on manipulator joint values, to be represented in the MRI image space. This makes it possible to render the location of the tool(s) held by the manipulator(s) in the MRI image space. Additionally, the location of the RF coil device and other structures may be defined so that collision detection can be performed to prevent a manipulator from contacting these structures.

1.0 Models

For each object (e.g., each manipulator, the first structure, and the second structure) a model that defines the 3D coordinates of the touch point features on that object within that object's respective coordinate system can be created (sometimes referred to as a touch point model for a given object). In some embodiments, each model can take the form of a data structure comprising a list of the 3D coordinates of each touch point on the object using that object's coordinate system. In some embodiments, a given object's coordinate system is common for all uses of that object. In the case of the first structure, for example, the 3D surface model of that structure (which can be displayed graphically), the touch point model for the first structure, and a model created using the 3D coordinates in first structure space of the markers (which can be MRI-visible markers) embedded in the first structure next to the touch point features on the first structure, are all expressed in the same coordinate system. In other embodiments, the touch point model and 3D surface model for a given object can be expressed in different coordinate systems provided the physical relationship between them is known or a transformation matrix relating the two exists.

Figure 5:
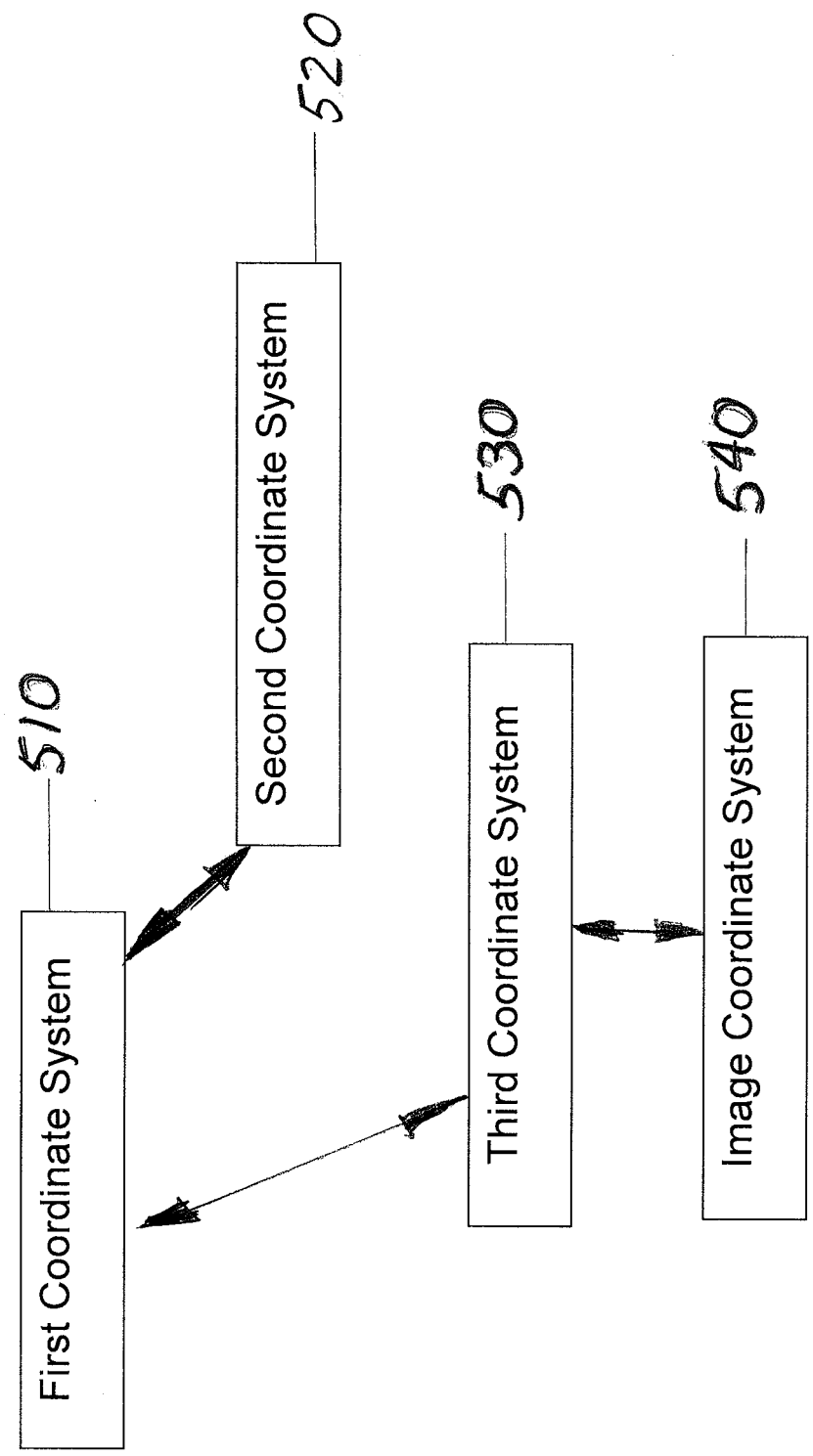
FIG. 5 is a schematic representation of various coordinate systems and calculated transformations between the coordinate systems.

Referring now to the figures, various coordinate systems involved in the performance of some embodiments of the present registration methods, devices, and systems are shown in FIG. 5. First coordinate system 510 is associated with registration tool 20 (see, e.g., FIGS. 1-3), second coordinate system 520 is associated with robotic arm 30 (see, e.g., FIGS. 2 and 3), third coordinate system 530 is associated with first structure 100 (shown throughout many of the figures), and magnetic resonance imaging coordinate system 540 is associated with the magnetic resonance image of first structure 100.

2.0 Touch Point Features and MR Markers 2.1. Arm Base Touch Point Features

In some embodiments, there are four touch point features on each of the manipulators, three on the base of the manipulator and a fourth on the top of the shoulder roll joint on the shoulder yaw axis of rotation. The fourth point is used for redundancy and to constrain the solution. Each touch point can be machined into the part as a cone shaped divot to accept the registration arm tip. Other embodiments may have other touch point features for interfacing to the registration arm tip, such as protrusions that engage a recess on the registration arm tip. Four features is the minimum number of features that can be used, and more may be used for additional redundancy or to constrain the solution for a manipulator with additional degrees of freedom. However, for a six degree of freedom manipulator it may be preferable to use no more than four features during the registration process to reduce the time required for the registration process. The touch point features can be positioned in an asymmetrical relationship with each other to minimize the number of touch point features that create a unique solution.

In other embodiments, four touch point features can be positioned on a structure that has a known relationship (e.g., a fixed relationship) with a given manipulator. For example, if a manipulator is secured in a fixed relationship to a mobile base, some of the four touch point features can be located on that mobile base.

2.2. Second Structure Secondary Target Touch Point Features

In some embodiments, there are four touch point features on the second structure (also referred to as a secondary target). The layout of the touch point features can be similar to that of the touch point features on a given manipulator. The secondary structure serves to provide a configurable position that is fixed to the first structure to accommodate re-registration if necessary. The secondary target 310 of one embodiment of the present registrations, systems, and methods, and the present RF coil devices is shown, for example, in FIGS. 1 and 3.

2.3. First Structure Touch Point Features and MR Markers

Figure 4:
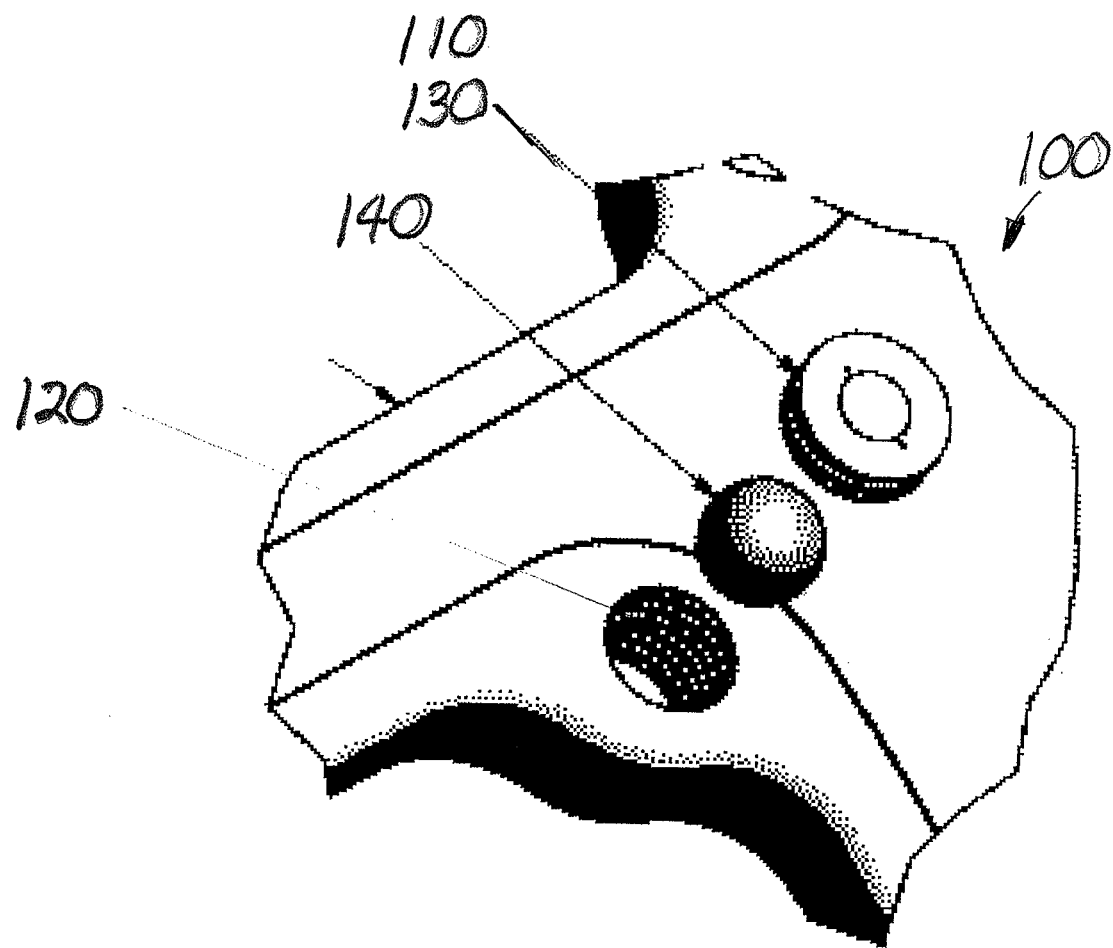
FIG. 4 is an assembly view of a portion of a structure that is attached to an RF coil, showing a marker that (in use) is embedded in the depicted recess of the structure, and a cap that contains a touch point feature. In use, the cap covers the marker and is secured to the structure using fasteners.

In some embodiments, the shape of the first structure entirely encloses an RF coil, and the first structure is configured such that the touch point features on the first structure are at a fixed distance to magnetic resonance imaging-visible marker 140 embedded in first structure 100, as show in exploded view in FIG. 4. Among suitable MR markers are spherical vitamin E capsules, which are highly visible on an MR image. The capsules are placed inside recess 120 in first structure 100. Recess 120 is then sealed using removable cap 130 that screws into first structure 100 and that includes touch point feature 110 on the top, exposed portion of the cap. As a result, the capsules can be replaced as necessary.

The placement of the first structure touch point features and MR markers is such that they are not symmetric, and the distances between most of the first structure touch point features is unique to aid in the identification of those distances. Numerous first structure touch point features, much greater than the number required in determination of a unique solution for the first structure, may be spread across the entire first structure so that sufficient points to accomplish registration are accessible regardless of the orientation of the first structure, surgical robot, and other objects within the operating room. An embodiment of device 10 having first structure 100 that has numerous touch point features 110 is depicted in FIG. 8.

3.0 Physical Registration Process

In some embodiments, the user will select all of the touch point features on all of the objects using a registration tool that is a high accuracy digitizer, such as the MicroScribe® MX registration arm available from Immersion Corporation. The registration tool can be positioned on a base to which the robotic arm(s) are secured. These touch point features are identified in the coordinate system of the registration tool (which may be referred to as a coordinate system associated with the registration tool). Thus, their positions are in the registration tool coordinate system.

Figure 2:
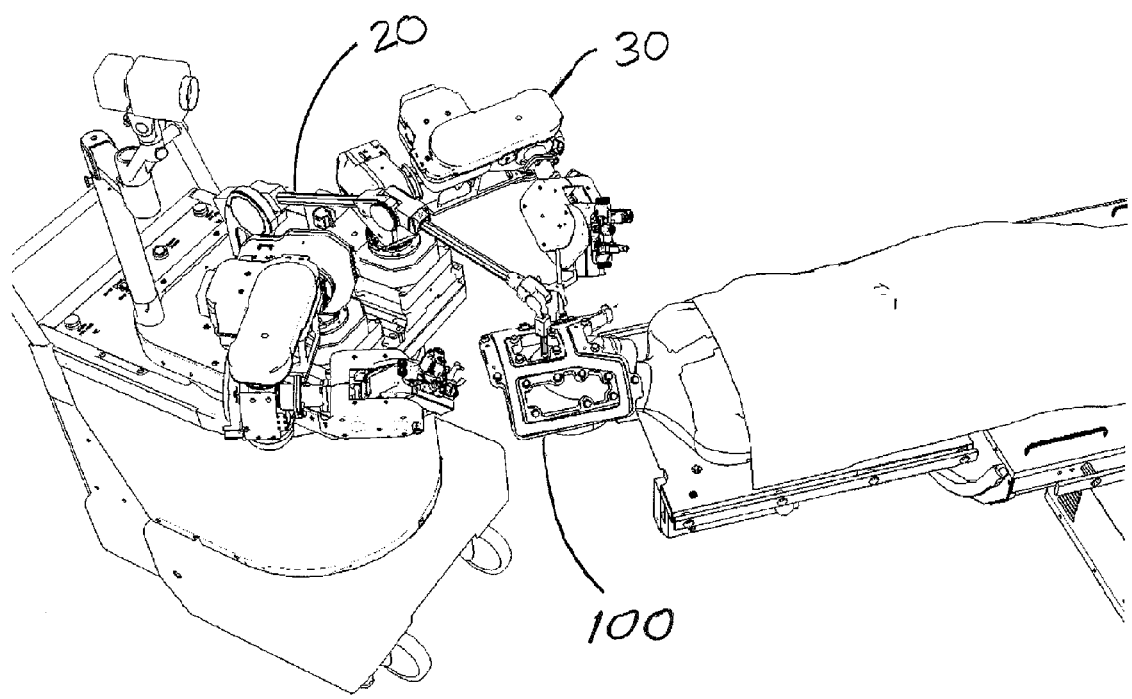
Figure 3:
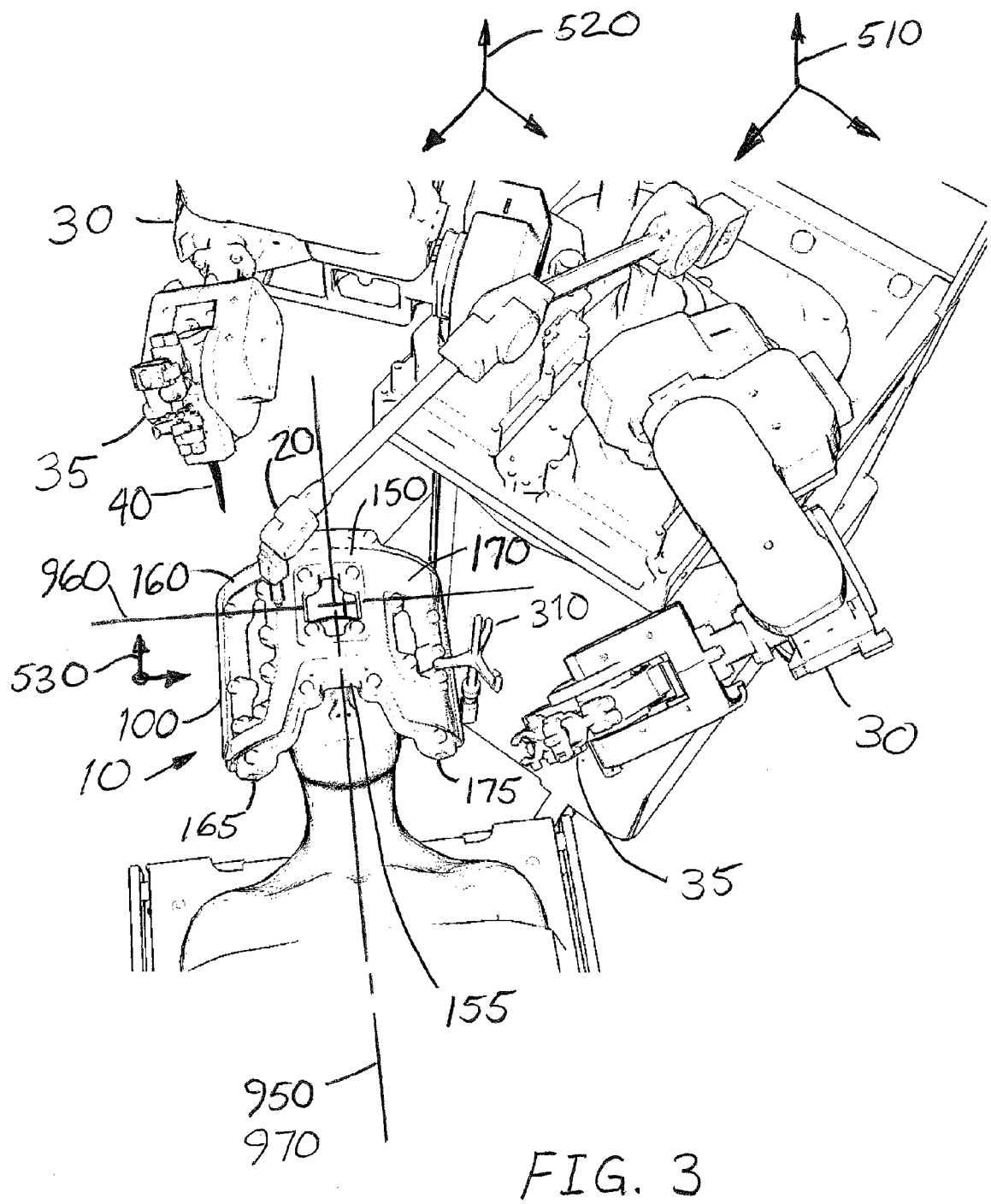

Referring to FIGS. 1-3, embodiments are depicted in which registration tool 20 is associated with first coordinate system 510. Referring to the embodiment depicted in FIG. 3, first coordinate system 510 is associated with registration tool 20, second coordinate system 520 is associated with robotic arm 30, and third coordinate system 530 is associated with first structure 100.

In some embodiments, the first step is to automatically locate the touch point features on the robotic arms from all of the touch point features collected using the registration tool. These robotic arm touch point features taken via the registration tool are then matched to the touch point model of a given robotic arm, so that the computer system correlates touch point features taken during physical registration with the corresponding touch point feature in the touch point model of the robotic arm. The transformation between the registration points (that is, the touch point features of the robotic arm taken using the registration tool) and the touch point model of the robotic arm is computed using a least squares algorithm or other regression method. This transformation represents the transformation from the registration arm coordinate system (sometimes referred to as a "frame") to the coordinate system of the respective robotic arm. Referring to FIG. 5, this transformation is depicted by the line between first coordinate system 510, associated with the registration arm, and second coordinate system 520, associated with a robotic arm.

In some embodiments, all remaining registration points (in other words, all remaining touch point feature positions identified using the registration tool) are transformed into a world coordinate system using a standard homogenous transformation matrix. The world coordinate system can be a coordinate system having a known relationship to the coordinate system of the coordinate systems of each respective robotic arm. This transformation is done so that any further least squares operations will yield a transformation between the world coordinate system and the coordinate system of the first structure or secondary target, respectively.

In some embodiments in which microsurgery will be performed, the touch point features from among those that are registered and that are on the secondary target are located using a matching process based on the distances between those touch point features. A transformation between the identified secondary target touch point features in world space and those same touch point features in the coordinate system of the secondary target can be computed using a least squares algorithm or other regression method. This transformation represents the transformation between the world coordinate system and the coordinate system of the secondary target. Though after the matching and before this transformation, the touch point features on the secondary target are known in the world coordinate system, this transformation permits the system to know the location and orientation of the secondary target to allow for collision detection to be accomplished relative to the secondary target. Furthermore, should the robotic arm move (such as by virtue of movement of the platform on which it is positioned), should the RF coil to which the first structure is attached be removed or moved, or should the secondary target move by virtue of movement of the head clamp to which it is attached in a fixed relationship, this transformation makes it possible to re-register the location of the secondary target (and therefore the head clamp that is fixed to the patient's head) using the registration tool such that the position of the other objects relative to the secondary target (and therefore the patient's head) can be known again.

In some embodiments, all remaining registration touch point features (which are those that do not include the matched manipulator touch point features or the matched secondary target touch point features) are matched to the touch point model of the first structure, so that the computer system knows which first structure registration point corresponds to which of the touch point features in the first structure's touch point model. The transformation between the first structure registration points (which can be in world frame, as explained above) and the frame of the first structure's touch point model may be calculated using a least squares algorithm or other regression method. Referring to FIG. 5, this transformation is depicted by the line between first coordinate system 510, associated with the registration arm, and third coordinate system 530, associated with the first structure.

3.1. Touch Point Feature Matching and Transformations

As explained above, in some embodiments, the registration touch point features that are collected are identified as being either manipulator touch point features, secondary target touch point features, or first structure touch point features using a matching process. In the case of the first structure, for both the touch point features and the MR markers, three points, the minimum number of points required to compute a unique homogenous transformation, are selected from all of the registration points. Which three registration points are selected is not relevant because if the three selected do not provide a solution the process will be repeated until all possible combinations are exhausted. The distances between these three selected points is calculated using a standard two norm calculation. These distances are then compared to the distances between all of the touch point features in the first structure touch point model until the three distances from the selected registration points and the matched three distances from the touch point model are within a tolerance. When a distance matching is found, a transformation between the three selected registration points and the three corresponding touch point features from the touch point model is calculated using a least squares algorithm or other regression method. Using this transformation, all remaining registration points identified on the first structure are then moved into the first structure's coordinate system (or whatever coordinate system was used to define the first structure's touch point model). Once the registration points are in a common coordinate system, another matching is performed between the transformed registration points and the touch point model for the first structure or a model of the MR marker locations in first structure coordinate space by locating matching points where the distance between them is below a threshold. The threshold is defined to be larger than the registration arm accuracy but not so large that the matching could select another nearby point. If the percentage of points matched in this process is below a threshold, the entire process is repeated using three other features until a valid match is found (assuming one exists).

4.0 MRI Registration

The first structure includes markers that are displayed in MRI images. These markers are selected by the user using a commercially-available MR image viewer. The user selects features by reviewing each image and designating areas that correspond to MR markers. The MR image viewer processes the user selection and detects the image pixels that have an intensity of an MR marker. This is performed in the image selected as well as in the neighboring images that represent corresponding cross-sectional planes at varying depth. This creates a 3D volume of the user selected marker. The centroid of this volume is calculated, representing the center of the MR marker in image space. The centroid of a given marker is used in the matching and transformations described below.

Once all the markers have been selected and centroids located, they are identified by matching them using the MR marker distances from the model for the MR markers. Once identified, the transformation between the position of the MR markers in image space and their position in the coordinate space of the model is calculated using a least squares algorithm or other regression method. This transformation yields a transformation between the first structure coordinate system and the MRI image space.

Figure 6:
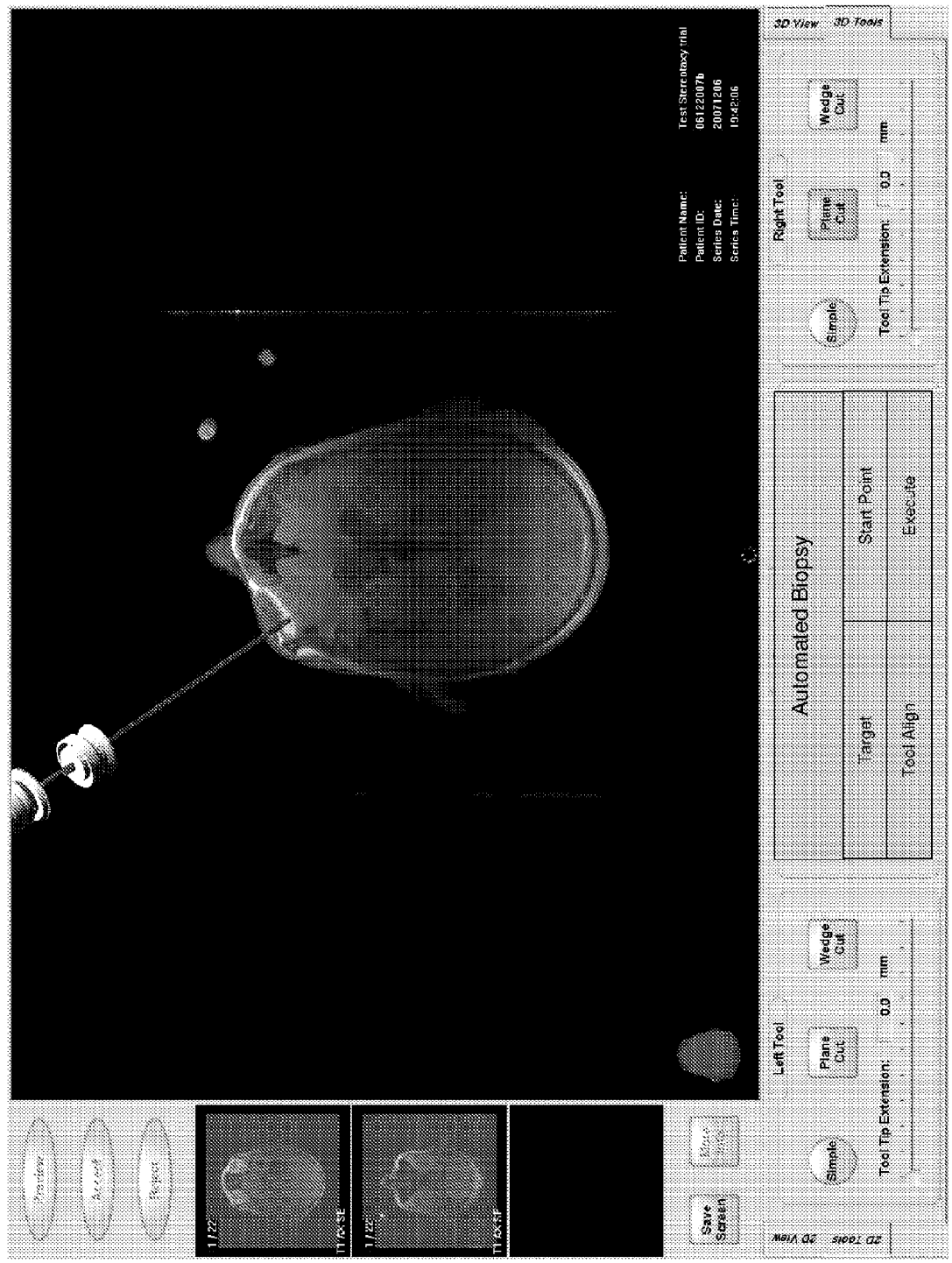
FIG. 6 depicts an overlay display that shows a representation of a surgical tool held by the robotic arm overlaying an image representative of a portion of the patient.

A view of the magnetic resonance image of first structure 100 is shown in FIG. 6. An image of a patient's head is visible in the middle of the view, and two magnetic resonance imaging-visible markers are visible slightly to the top-right of the head. A transformation between third coordinate system 530, associated with first structure 100, and magnetic resonance imaging coordinate system 540, associated with the magnetic resonance image of first structure 100, is computed by (1) correlating the magnetic resonance imaging-visible markers 140 expressed in the magnetic resonance imaging coordinate system with the corresponding touch point features expressed in the magnetic resonance imaging coordinate system, and (2) computing a transformation between the positions of the multiple touch point features expressed in the third coordinate system and the positions of the multiple touch point features expressed in the image coordinate system.

Returning to FIG. 5, the transformation between third coordinate system 530, associated with first structure 100, and magnetic resonance imaging coordinate system 540, associated with the magnetic resonance image of first structure 100, is depicted by the line between third coordinate system 530 and magnetic resonance imaging coordinate system 540. Transformations between all coordinate systems depicted in FIG. 5 are known, and therefore transformation of position data expressed in any of the coordinate systems can be transformed to any other coordinate system. For instance, robotic arm position data expressed in second coordinate system 520 may be transformed to position data expressed in the image coordinate system by using a series of transformations to transform the expression of the data from second coordinate system 520 to first coordinate system 510 to third coordinate system 530, and finally to magnetic resonance imaging coordinate system 540.

4.1. MR Touch Point Feature Matching

In some embodiments, the MR touch point matching algorithm is substantially the same as the algorithm used for both the manipulator touch point features and the secondary target touch point features. First, the algorithm is applied using all registration points to find the manipulator touch point features (one set for stereotaxy and two sets for microsurgery). Then, the found manipulator touch point features are flagged and are not used in the next step: identifying the secondary target touch point features. The following description outlines an example process:

1. calculate the distances between all point pairs in the model;
2. pick up the first 3 largest distances representing the distances between the top point feature (that is, the top touch point feature) and the rest of the points in the model (the bottom one and the side ones);
3. calculate the cosine defined of the angle defined by the following 2 vectors: top point feature-bottom point feature and top point feature-side point feature;

4. search the collected physical point set (the touch point features collected using the registration tool) for any point that has the similar distances to other points (within a tolerance) to the ones selected at step 2;
5. verify that the corresponding cosine is close (within a tolerance) to the one from step 3;
6. if both steps 4 and 5 are valid, consider a candidate match and apply a best-fit algorithm for the model points and the candidate match set;
7. if the best-fit algorithm returns an error smaller than a defined threshold, this is a match;
8. if the algorithm is used for a manipulator in stereotaxy or for the secondary target, just one match is expected. The transformation is calculated and stored using this unique match;
9. if the algorithm is used for both manipulators in microsurgery, two matches are expected. In this case, there are additional steps for identifying the right and the left manipulator touch point features:
    9.1 consider the vector defined by the top and the bottom touch point features from one matched set;
    9.2 calculate how many points from both matched sets are on the left and on the right of this vector using the order (clockwise/counterclockwise) of all combinations of three points (top, bottom and every other point);
    9.3 if there is only one point on its right, the top-bottom points belong to the right manipulator (e.g., the base of the right manipulator);
    9.4 if there is only one point on its left side, the top-bottom points belong to the left manipulator (e.g., the base of the left manipulator);
    9.5 calculate and store the transformation using only the right manipulator touch point features.

Embodiments of the present methods may be coded as software stored on any suitable computer readable media (e.g., tangible computer readable media), such as any suitable form of memory or data storage device, including but not limited to hard drive media, optical media, RAM, SRAM, DRAM, SDRAM, ROM, EPROM, EEPROM, tape media, cartridge media, flash memory, memory stick, and/or the like. Tangible computer readable media includes any physical medium that can store or transfer information. Such embodiments may be characterized as tangible computer readable media having (or encoded with) computer executable (e.g., machine readable) instructions for performing certain step(s). The term "tangible computer readable medium" does not include wireless transmission media, such as carrier waves. The term "computer readable medium," however, does cover wireless transmission media, and some embodiments of the present methods may include wireless transmission media carrying the computer readable instructions described above. The software can be written according to any technique known in the art. For instance, the software may be written in any one or more computer languages (e.g., ASSEMBLY, PASCAL, FORTRAN, BASIC, C, C++, C#, JAVA, Perl, Python) or using scientific packages like, but not limited to, Matlab®, R, S-plus®, and SAS®. The code may be to enable it to be compiled on all common platforms (e.g., Microsoft®, Linux®, Apple Macintosh® OS X, Unix®). Further, well-established cross-platform libraries such as OpenGL® may be utilized to execute embodiments of the present methods, devices and systems. Multi-threading may be used wherever applicable to reduce computing time on modern single- and multi-processor based hardware platforms. As discussed above and illustrated in the figures, the software may include a GUI, which may provide a user with a more intuitive feel when running the software. Different fields may be accessible by screen touching, a mouse and/or keyboard. Alarms, cues, and the like may be done via pop-up windows, audible alerts, or any other techniques known in the art.

Some (up to all) of the steps described in the sections above may be implemented using a computer having a processor (e.g., one or more integrated circuits) programmed with firmware and/or running software. Some (up to all) of the steps described in the sections above may be implemented using a distributed computing environment, which is one example of a computer system. In a distributed computing environment, multiple computers may be used, such as those connected by any suitable number of connection mediums (e.g., a local area network (LAN), a wide area network (WAN), or other computer networks, including but not limited to Ethernets, enterprise-wide computer networks, intranets and the Internet, and the connections between computers can be wired or wireless). Servers and user terminals can be part of a given computer system. Furthermore, embodiments of suitable computer systems may be implemented on application specific integrated circuits (ASICs) or very large scale integrated (VLSI) circuits, and further (or alternatively) may be configured to use virtualization of resources, virtual computing, and/or cloud computing to achieve the specified functions. In fact, persons of ordinary skill in the art may utilize any number of suitable structures capable of executing logical operations in order to achieve the functions described above in a computer system consistent with this disclosure.

5.0 RF Coil Device

Figure 7:
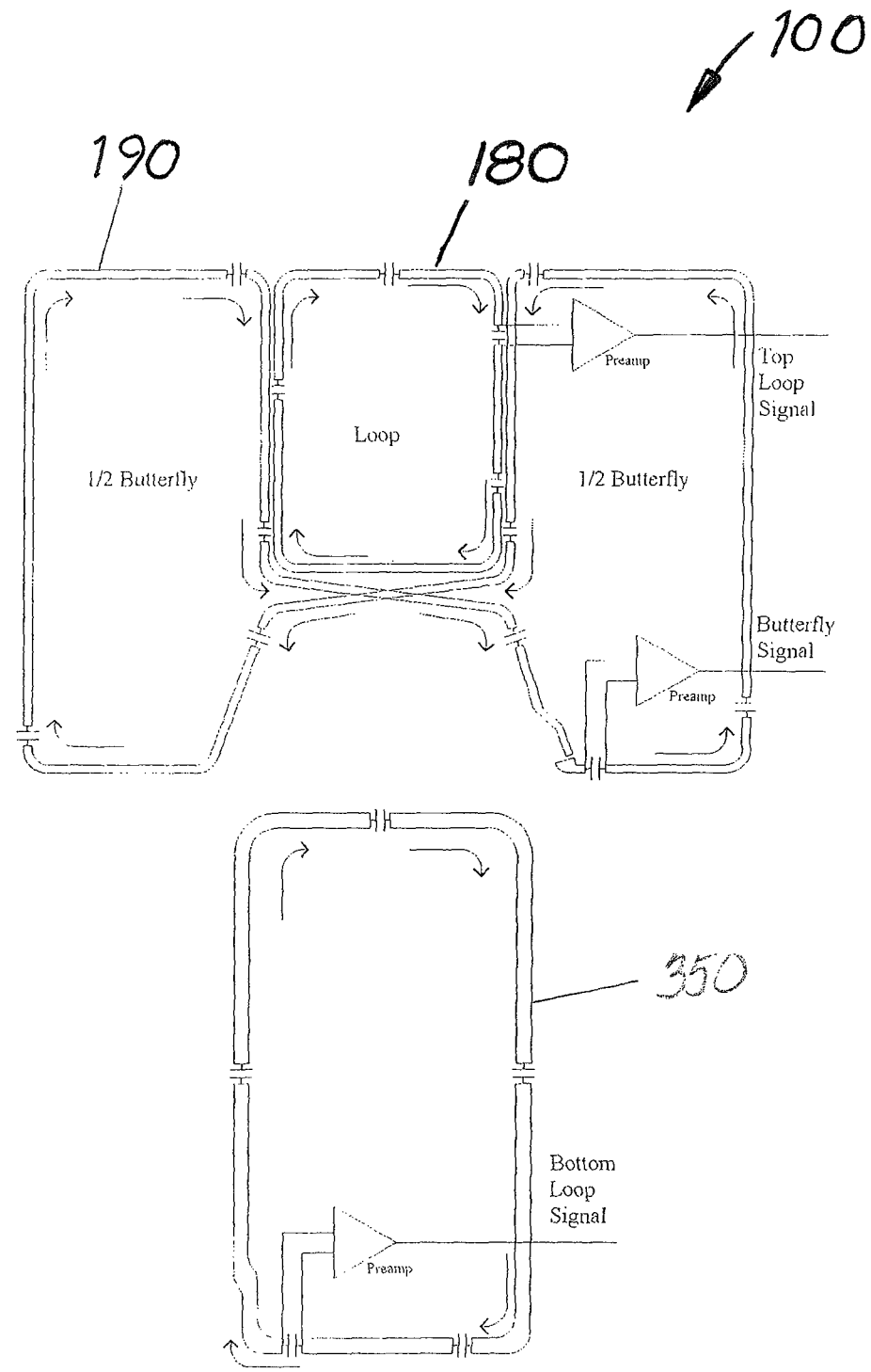
FIG. 7 is a schematic depicting RF coils that are present in some embodiments of the present RF coil devices.

Embodiments of the present RF coil devices provide for focused signal-to-noise performance in magnetic resonance imaging. FIG. 7 is a schematic of the RF coils present in an embodiment of the present RF coil devices. Second radiofrequency coil 180 is a smaller RF coil than radio frequency (RF) coil 190, giving rise to better signal-to-noise performance (or a better signal-to-noise ratio (SNR) performance), and therefore higher image resolution, than that achieved by the larger RF coil 190. Second RF coil 180 is positioned in the center region of first structure 100, preferably allowing for positioning of second RF coil 180 near the region of interest on the patient. The larger RF coils—RF coil 190 (located in first structure 100) and lower RF coil 350 (located in lower structure 300)—provide for imaging a larger area than that covered by second RF coil 180, but with a lower signal-to-noise ratio. This diversity of RF coils within the RF coil device allows for focused signal-to-noise performance, where high resolution may be delivered in the region of interest while minimizing the number of RF coils needed to fully cover a larger area at lower resolution.

FIGS. 8A and 8B provide two perspective views of an embodiment of device 10. Device 10 may be referred to more specifically as RF coil device 10. FIG. 8B depicts the same embodiments as FIG. 8A rotated 180 degrees. Device 10 includes first structure 100 and lower structure 300. Located in multiple locations on first structure 100 are magnetic resonance imaging-visible markers (show as markers 140 in FIG. 4), and located on first structure 100 are multiple touch point features 110. MRI-visible markers 140 and touch point features 110 have a fixed spatial relationship, and facilitate registration by MRI and physical registration methods of device 10 and robotic arm 30 to a patient fixed to device 10. MRI-visible markers 140 and removable cap 130 may be configured as depicted in FIG. 4, including recess 120 and removable cap 130 designed such that sterilization of device 10 will not result in penetration to recess 120 by materials that may degrade MRI-visible markers 140. Suitable sterilization of device 10 allows for placement of the device proximate a patient's head during stereotaxy such that, for example, the portion of the device closest to the open lesion (e.g., formed through a craniotomy or a burr hole) is less than 50 centimeters from the lesion in some embodiments, less than 40 centimeters in some embodiments, less than 30 centimeters in some embodiments, less than 20 centimeters in some embodiments, less than 10 centimeters in some embodiments, and about 5 centimeters in some embodiments.

Some embodiments of device 10 may be sterilized using the hydrogen peroxide gas plasma process of the STER-RAD® 100S Sterilizer from Advanced Sterilization Products (which is an example of the type of sterilization process device 10 may be configured to withstand to enable it to be placed proximate an open lesion as described above) without adversely affecting the performance of RF coil 190, second RF coil 180, lower RF coil 300, MRI-visible markers 140, or other components of device 10. In these embodiments, the materials of first structure 100 and lower structure 300 will not be damaged by the process, which involves subjecting device 10 to a vacuum (400 mTorr) and then to hydrogen peroxide plasma ($H_2O_2$ plasma activated with 400 W RF power at about 500 mTorr for about 17 minutes). This vacuum subjection and hydrogen peroxide plasma exposure process may then be repeated again.

Some embodiments of device 10 further include attachment mechanism 200, which provides first structure 100 with adjustment in at least four degrees of freedom of movement. Attachment mechanism 200 may include translation bracket 210 fixed to first structure 100, vertical strut 220 coupled to translation bracket 210, and upper arch 230 coupled to vertical strut 220 and to lower structure 300.

In some embodiments, the four degrees of freedom available for adjustment of first structure 100 include translation in the head-foot direction (which may be referred to as superior-inferior translation), translation in the up-down direction (which may be referred to as anterior-posterior translation), movement comprising azimuthal rotation, and movement comprising tilting.

FIGS. 9A and 9B depict translation of first structure 100 in the head-foot direction. This adjustment involves linear translation of translation bracket 210 relative to vertical strut 220. Strut 220 includes two channels 222 in which bracket rails 212 can travel in the head-foot direction when cam lever mechanism 227, which includes a pin extending from one side of strut 220 to the other through side channel 214 in bracket 210, is released. Mechanical mechanisms other than cam lever mechanism 227 may be used in other embodiments to facilitate the depicted movement between bracket 210 and strut 220 and lock them in place.

Figure 10B:
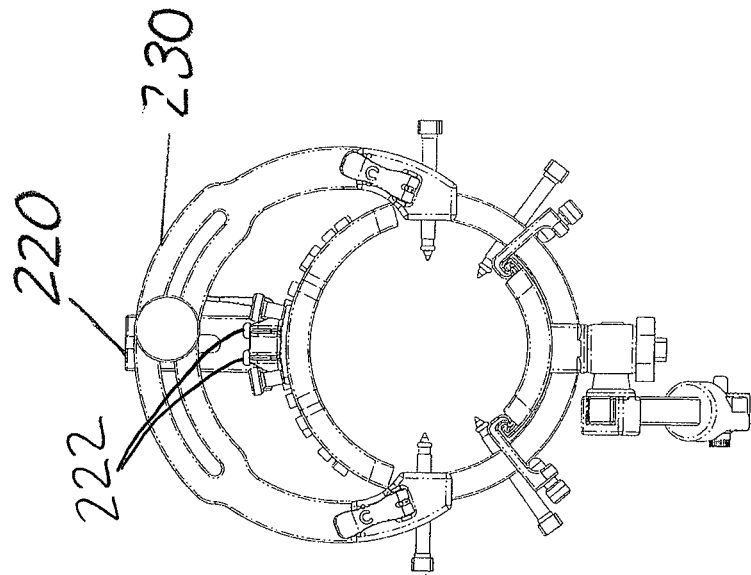
FIGS. 10A and 10B depict adjustment of an RF coil device in which the first structure is translated in the up-down direction.
Figure 10A:
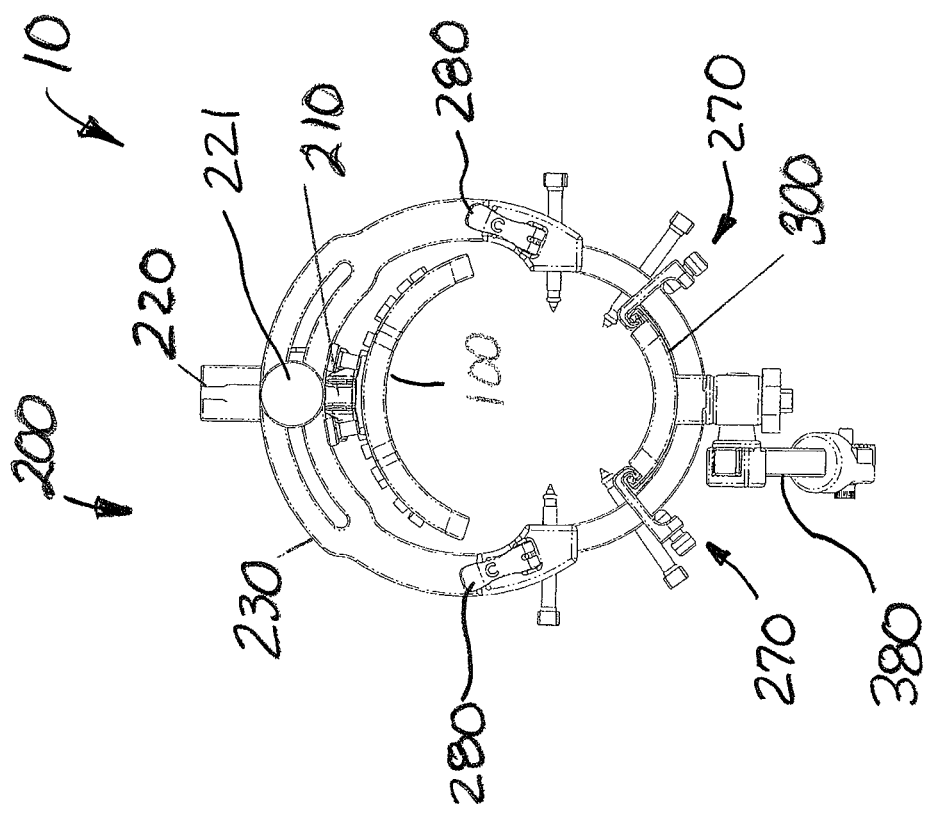

FIGS. 10A and 10B depict translation of first structure 100 in the up-down direction. This adjustment involves linear translation of vertical strut 220 relative to upper arch 230 that may be achieved in part through releasing and tightening thumb screw 221. Mechanical mechanisms other than thumb screw 221 may be used in other embodiments to facilitate the depicted movement between and lock these parts in place.

FIGS. 11A and 11B depict movement of first structure 100 involving azimuthal rotation, or rotation about an axis that is substantially parallel to the body centerline of a patient when the patient's head is fixed to device 10. This adjustment involves angular displacement of the vertical strut 220 relative to the upper arch 230 that may be achieved in part through releasing and tightening thumb screw 221. Mechanical mechanisms other than thumb screw 221 may be used in other embodiments to facilitate the depicted movement between and lock these parts in place.

FIGS. 12A and 12B depict movement of first structure 100 involving tilting, or rotation about an axis that is substantially parallel to an axis that runs from one ear to the other ear of a patient when the patient's head is fixed to device 10. This adjustment involves angular displacement of translation bracket 210 relative to vertical strut 220. This adjustment may be achieved using, in part, cam lever mechanism 227. The angular displacement is possible because the top portions of channels 222 (see FIGS. 8A and 10B) are sufficiently larger than bracket rails 212 to allow the bracket rails to tilt within channels 222. Mechanical mechanisms other than cam lever mechanism 227 may be used in other embodiments to facilitate the depicted movement between bracket 210 and strut 220 and lock them in place.

FIGS. 9A-12B also show that device 10 is configured to be attached to a head clamp, such as head clamp 380, and reflect that some embodiments of the present devices comprise both an RF coil device and a head clamp. The attachment may be a non-permanent one, and may be achieved using a head clamp attachment system that includes head clamp attachment cam lever elements 280 and lower elements 270, each of which includes brackets 272 coupled to lower structure 300 and thumb screws 278 threaded through openings in brackets 272. Mechanical mechanisms other than elements 270 and 280 may be used in other embodiments to couple device 10 to a given head clamp.

Figure 13:
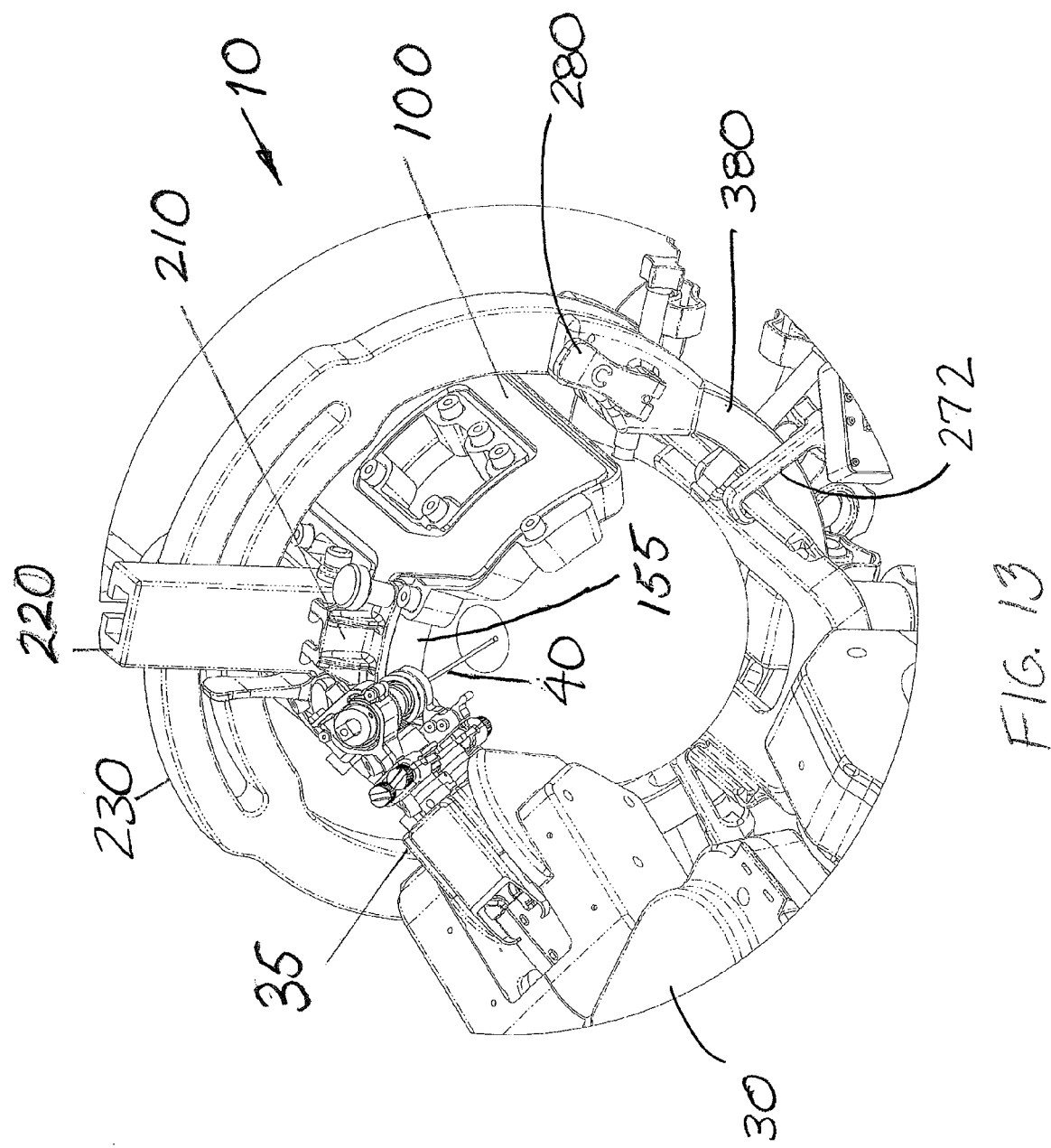
FIG. 13 depicts a robot performing surgery on a patient's head that is fixed to an RF coil device.

FIG. 13 depicts the use of an embodiment of device 10 fixed to the head of a patient via head clamp 380, where the patient is undergoing a stereotactic surgical procedure performed by a robot (more specifically a robotic arm). Surgical tool 40, coupled to end effector 35 of robotic arm 30, is gaining access to a portion of the patient's head in the area near middle section end surface portion 155 of first structure 100. The shape of first structure 100 provides an area near second RF coil 180 for access by surgical tool 40. Referring to FIG. 1, this area is near middle section 150, and is bordered by middle section end surface portion 155. FIG. 3 also shows the accessible area defined by middle section end surface portion 155, which is positioned nearer latitudinal plane 960 than is left section end surface portion 165 of left section 160 or right section end surface portion 175 of right section 170. Latitudinal plane 960 is normal to longitudinal plane 950. Longitudinal plane 950 is substantially parallel to patient's centerline 970, and intersects middle section 150.

One of ordinary skill in the art will appreciate that materials used in components of device 10 should be suitable for use within an MRI environment. For example, materials well-suited for first structure 100 and components of attachment mechanism 200 include Polypropylene and Polyvinyl Chloride Type 1, respectively. Titanium is well suited for use areas where higher strength is needed, such as fasteners.

Descriptions of well known processing techniques, components and equipment have been omitted so as not to unnecessarily obscure the present methods, devices and systems in unnecessary detail. The descriptions of the present methods, devices and systems are exemplary and non-limiting. Certain substitutions, modifications, additions and/or rearrangements falling within the scope of the claims, but not explicitly listed in this disclosure, may become apparent to those of ordinary skill in the art based on this disclosure. For example, the present registration methods may be used to register a patient to a robotic arm other than those shown in the figures and in the '316 patent. Furthermore, it will be appreciated that in the development of a working embodiment, numerous implementation-specific decisions must be made to achieve the developers' specific goals, such as compliance with system-related and business-related constraints, which will vary from one implementation to another. While such a development effort might be complex and time-consuming, it would nonetheless be a routine undertaking for those of ordinary skill in the art having the benefit of this disclosure.

The appended claims are not to be interpreted as including means-plus-function limitations, unless such a limitation is explicitly recited in a given claim using the phrase(s) "means for" and/or "step for," respectively.

The invention claimed is:

1. A system for registering a three-dimensional volume of a portion of a patient to a robotic arm, the system comprising:
   a. at least one robotic arm configured for manipulating a surgical instrument;
   b. a registration tool;
   c. a plurality of first touch point features configured to interface with the registration tool, each of the first touch point features having a fixed spatial relationship with the robotic arm;
   d. a plurality of markers;
   e. a plurality of second touch point features configured to interface with the registration tool, each of the second touch point features having a fixed spatial relationship with at least one of the plurality of markers;
   f. a first structure configured for releasable association with the patient, the first structure configured for association with the markers and to provide one or more of the second touch point features; and
   g. a computer system configured for computing a transformation for determining a position of the robotic arm relative to the three-dimensional volume of the patient based on positions of the first and second touch point features and the fixed spatial relationships of the touch point features with the robotic arm and the markers.

2. The system according to claim 1, configured for operation in combination with a magnetic resonance (MR) imaging system, wherein the markers are MR-visible markers.

3. The system according to claim 1, wherein the transformation for determining the position of the robotic arm relative to the three-dimensional volume of the patient is further based on positions of one or more of the markers as identified in an image coordinate system.

4. The system according to claim 1, wherein one or more of the first touch point features are disposed on the robotic arm.

5. The system according to claim 4, wherein at least four first touch point features are disposed on the robotic arm.

6. The system according to claim 1, further comprising a second structure releasably attached to the first structure, wherein one or more of the second touch point features are provided by the second structure.

* * * * *